United States Patent [19]
Aoyama et al.

[11] Patent Number: 5,851,785
[45] Date of Patent: Dec. 22, 1998

[54] METHOD OF QUANTITATIVE DETERMINATION OF SUBSTANCES USING COUMARIN DERIVATIVES

[75] Inventors: Norihito Aoyama; Hideki Takenaka; Akira Miike, all of Shizuoka, Japan

[73] Assignee: Kyowa Medex Co., Ltd., Tokyo, Japan

[21] Appl. No.: 288,738

[22] Filed: Aug. 16, 1994

Related U.S. Application Data

[63] Continuation of Ser. No. 122,582, filed as PCT/JP93/00128, Feb. 3, 1993 published as WO93/15219, May 8, 1993, abandoned.

[30] Foreign Application Priority Data

Feb. 4, 1992 [JP] Japan ................... 4-019043

[51] Int. Cl.$^6$ ........................................ C12Q 1/28
[52] U.S. Cl. ................................ 435/28; 435/7.93
[58] Field of Search ................... 435/7.93, 968, 435/28

[56] References Cited

U.S. PATENT DOCUMENTS

| | | | |
|---|---|---|---|
| 4,853,328 | 8/1989 | Okazaki et al. | 435/805 |
| 4,857,455 | 8/1989 | Khanna et al. | 435/968 |

FOREIGN PATENT DOCUMENTS

| | | |
|---|---|---|
| 110682 | 6/1984 | European Pat. Off. . |
| 121743 | 10/1984 | European Pat. Off. . |

OTHER PUBLICATIONS

J. De la Harpe et al., J. Immunolg. Meth., vol. 78, pp. 323–336 (1985).
A. Boveris et al., Analyt. Biochem., vol. 80, pp. 145–158 (1977).
P. Laing, J. Immunolog. Methods, vol. 92, pp. 161–165 (1986).
J. Roberts et al., J. Immunolog. Methods, vol. 143, pp. 49–56 (1991).
D. Slawinska et al., J. of Luminescence, vols. 40&41, pp. 262–263 (1988).
D. Slawinska et al., Internat'l. Symp. on Analyt. Applications of Biolumin. and Chemilumin., Proceedings, pp. 239–257 (1979).
V. de Sandro et al., Analyt. Biochem., vol. 206, pp. 408–413 (1992).
L. Holm et al., Anal. Chem., vol. 59, pp. 582–586 (1987).
Slawinska et al., J. Biolumin Chemilumin, vol. 4, No. 1 (1989) 226–230.
Xie et al., Fenxi Huaxue, vol. 19, No. 7 (1991) 823–825.
Tod et al., J. Chromatogr., vol. 542, No. 2 (1991) 295–306.
Imai, Bioluminescence & Chemiluminescence, Luminol Derivatives (1989)82–89, (Japanese).
Fluorometric Analytical Chemistry (1987) 159–161 (Japanese).
J. of Jap. Chem. Assn. vol. 3 (1972) 644–648 (Japanese).
Chen et al., Heterocycles, vol. 7, No. 2 (1977) 933–945.
J. of Ind. Chem., vol. 71 (1968) 1010–1015. (Japanese).
Catalog of Eastman Kodak Co. (Coumarin).
Catalog of Wako Pure Chemicals Co. (Fluorescent Probes).

*Primary Examiner*—Mary E. Ceperley
*Attorney, Agent, or Firm*—Fitzpatrick, Cella, Harper & Scinto

[57] ABSTRACT

The present invention relates to a method for quantitatively determining a peroxidation-active substance, hydrogen peroxide or a coumarin derivative represented by formula (I) or (II):

wherein $R^1$, $R^2$, $R^3$, $R^4$, $R^5$ and $R^6$ are the same or different and each represents hydrogen, substituted or unsubstituted lower alkyl, substituted or unsubstituted aralkyl, substituted or unsubstituted aryl or halogen; the method comprising reacting the hydrogen peroxide with the coumarin derivative represented by formula (I) or (II) or its salt in the presence of the peroxidation-active substance, and determining the amount of the light emission or the light intensity from the reaction solution.

35 Claims, 4 Drawing Sheets

CEA CONTENT (ng/nl)

AEP CONTENT (ng/ml)

METHOD OF QUANTITATIVE DETERMINATION OF SUBSTANCES USING COUMARIN DERIVATIVES

This application is a continuation of application Ser. No. 08/122,582, filed as PCT/JP93/00128, Feb. 3, 1993 published as WO93/15219, May 8, 1993, now abandoned.

TECHNICAL FIELD

The present invention relates to a method for quantitative determination of peroxidation-active substances, hydrogen peroxide and a coumarin derivative of the formula (I) or (II) as described hereinafter, by chemiluminescence using coumarin derivatives.

BACKGROUND ART

Accurate quantitative determination of an extremely trace amount of hydrogen peroxide or peroxidase activity is important in analytical chemistry and biological chemistry. In particular, in the field of clinical inspections, various means have been employed in which a substance to be analyzed or determined is converted into hydrogen peroxide, and the converted hydrogen peroxide is determined for the quantitative determination of the substance. Methods of quantitative determination of antigens, antibodies or DNA's have been known, in which an antigen, antibody or DNA is labeled with a peroxidase, an oxidase other than peroxidase or a luminous compound; and the peroxidase activity or the amount of the hydrogen peroxide or the luminous compound to be formed by reaction of the oxidase is quantitatively determined.

Of methods of quantitative determination of hydrogen peroxide or a peroxidase activity, a method of utilizing bioluminescence or chemiluminescence of the compound to be used as a substrate for peroxidase is known as a high-sensitive determination method. As the preferred luminous compounds, there are known luminol, isoluminol, lucigenin, acridinium esters, etc. (Bioluminescence and Chemiluminescence, edited by Kazuhiro Imai; pp. 82–89 (1989), published by Hirokawa Books Co.). However, the method has a problem that the emission intensity is lowered when the reaction solution contains proteins or the reaction solution is in an acidic pH range.

Coumarin derivatives represented by the formulae (I) and (II) as described hereinafter are known as fluorescent compounds and are commercially available (Fluorometric Analytical Chemistry, 159–161 (1987), published by Baifukan Co.; Journal of Japan Chemical Association, 3, 644 (1972); Heterocycles, 7, 933 (1977); Journal of Industrial Chemistry, 71, 1010 (1968); Catalogs of Eastman Kodak Co. and Wako Pure Chemicals Co., etc.).

It is not known that coumarin derivatives emit light by hydrogen peroxide in the presence of a peroxidation-active substance.

DESCRIPTION OF THE INVENTION

The present invention relates to a method for quantitative determination of a peroxidation-active substance, hydrogen peroxide or a coumarin derivative represented by formula (I) or (II):

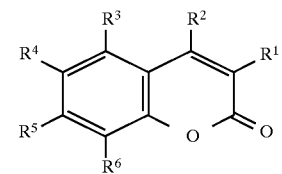

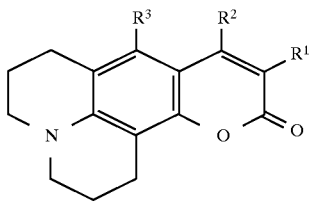

wherein $R^1$, $R^2$, $R^3$, $R^4$, $R^5$ and $R^6$ are the same or different and each represents hydrogen, substituted or unsubstituted lower alkyl, lower alkoxy, substituted or unsubstituted aralkyl, substituted or unsubstituted aryl, halogen, cyano, nitro, sulfo, carboxyl, alkoxycarbonyl, alkylcarbamoyl, substituted or unsubstituted arylcarbamoyl, carbamoyl, hydroxy, substituted or unsubstituted amino, lower alkanoyl, lower alkanoyloxy, or a heterocyclic group; or $R^1$ and $R^2$, combined together, form alkylene or alkenylene; or $R^4$ and $R^5$, combined together, form —$CH_2CH_2CH_2NH$—; the method comprises reacting the hydrogen peroxide with the coumarin derivative represented by formula (I) or (II) or with its salt in the presence of the peroxidation-active substance, and determining the amount of the light emission or the light intensity from the reaction solution.

The principle of the present invention is based on the fact that the above-mentioned reaction goes on stoichiometrically and that the amount of the light emission or the light intensity from the reaction solution is proportional to the amount of the peroxidation-active substance, hydrogen peroxide or a coumarin derivative used.

Although it has not been clarified what structure the coumarin derivative is converted to by the reaction, the existence of a substance differentiated from the starting coumarin derivative before the reaction was confirmed by chromatography, from which it is obvious that certain compound emitting light is formed by the reaction.

In the definitions of formulae (I) and (II), the alkyl moiety in the lower alkyl, lower alkoxy, lower alkanoyl, lower alkanoyloxy, alkoxycarbonyl and alkylcarbamoyl is a linear or branched alkyl having 1 to 8 carbon atoms, including, for example, methyl, ethyl, propyl, isopropyl, butyl, tert-butyl, pentyl, hexyl, heptyl and octyl; the aralkyl is one having 7 to 15 carbon atoms, including, for example, benzyl and phenethyl; the aryl moiety in the aryl and arylcarbamoyl is, for example, phenyl or naphthyl; the halogen includes iodine, bromine, chlorine and fluorine; and the heterocyclic group includes, for example, pyridyl and benzothiazolinyl.

The number of the substituents in the substituted alkyl, substituted aralkyl, substituted aryl and substituted arylcarbamoyl is 1 to 5. The substituents may be the same or different and selected from cyano, halogen, substituted or unsubstituted amino, lower alkyl, lower alkoxy, carboxy, alkoxycarbonyl and hydroxy. The alkyl moiety in the lower alkyl, lower alkoxy and alkoxycarbonyl and the halogen have the same meanings as mentioned above.

The number of the substituents in the substituted amino is 1 or 2. The substituents may be same or different and selected from lower alkyl and substituted or unsubstituted heterocyclic group. The lower alkyl has the same meaning as mentioned above; and the heterocyclic group includes, for example, triazinyl, pyrazinyl, pyridyl and pyrimidinyl. The number of the substituents in the substituted heterocyclic group is 1 or 2. The substituents may be the same or different and selected from cyano, halogen, amino, lower alkoxy, hydroxy and dialkylamino. The alkyl moiety in the lower alkoxy and alkylamino has the same meaning as mentioned above.

The alkylene has 2 to 4 carbon atoms, including, for example, —(CH$_2$)$_2$—, —(CH$_2$)$_3$— and —(CH$_2$)$_4$—. The alkenylene group has 2 to 4 carbon atoms, including, for example, —CH=CH—, —CH=CH—CH$_2$— and —CH=CH—CH=CH—.

As the acceptable salt of Compound (I) or (II), mention may be made of acid addition salts, including, for example, inorganic acid addition salts such as hydrochloride, sulfate or phosphate and organic acid addition salts such as acetate, maleate, fumarate or citrate.

Specific examples of the coumarin derivatives for use in the present invention are shown in Table 1.

TABLE 1

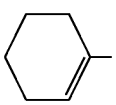

(I)

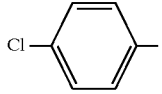

(II)

| Com-pound | Skel-eton | R$^1$ | R$^2$ | R$^3$ | R$^4$ | R$^5$ | R$^6$ |
|---|---|---|---|---|---|---|---|
| 1 | I | 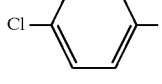 | H | H | H | NH$_2$ | H |
| 2 | I | H | CH$_3$ | H | H | NH$_2$ | H |
| 3 | I | CN | H | H | H | N(CH$_3$)$_2$ | H |
| 4 | I | 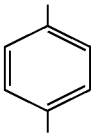 | CH$_3$ | H | H | N(CH$_3$)$_2$ | H |
| 5 | I | 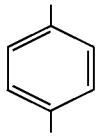 | H | H | H | N(C$_2$H$_5$)$_2$ | H |
| 6 | I | 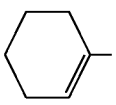 | H | H | H | N(C$_2$H$_5$)$_2$ | H |
| 7 | I |  | H | H | H | N(C$_2$H$_5$)$_2$ | H |
| 8 | I | H | CH$_3$ | H | H | N(C$_2$H$_5$)$_2$ | H |
| 9 | I |  | CH$_3$ | H | H | N(C$_2$H$_5$)$_2$ | H |

TABLE 1-continued (I) [structure: substituted benzene with R3, R4, R5, R6 on ring; R2 on vinyl; R1 on C=O]

(II) [structure: julolidine-fused coumarin with R3, R2, R1 substituents]

| Compound | Skeleton | R¹ | R² | R³ | R⁴ | R⁵ | R⁶ |
|---|---|---|---|---|---|---|---|
| 10 | I | OCH₃ (4-methoxyphenyl) | CH₃ | H | H | N(C₂H₅)₂ | H |
| 11 | I | α | CH₃ | H | H | N(C₂H₅)₂ | H |
| 12 | I | CN | H | H | H | NO₂ | H |
| 13 | I | H | CH₃ | H | OH | C₄H₉ | H |
| 14 | I | 3-cyanophenyl | H | H | H | OCH₃ | H |
| 15 | I | phenyl-NH-CO- | H | H | H | COOCH₃ | H |
| 16 | I | H | CH₃ | H | OH | COOCH₃ | H |
| 17 | I | cyclohexenyl | H | H | β | H | H |
| 18 | I | H | CH₃ | H | H | OH | H |
| 19 | I | Cl | CH₃ | H | H | OH | H |
| 20 | I | H | CH₃ | H | H | OH | NH₂ |
| 21 | I | CH₃ | CH₃ | H | H | OH | CH₃ |
| 22 | II | —CH₂CH₂CH₂— | | H | — | — | — |
| 23 | II | CN | H | H | — | — | — |
| 24 | I | H | CH₃ | H | CH₃ | NHC₂H₅ | H |
| 25 | I | H | CH₃ | H | H | OH | H |
| 26 | I | benzothiazolyl-cyclohexenyl | H | H | H | N(C₂H₅)₂ | H |
| 27 | II | H | CH₃ | H | — | NH₂ | H |
| 28 | I | H | CF₃ | H | H | NH₂ | H |
| 29 | I | H | CF₃ | H | H | N(CH₃)₂ | H |
| 30 | II | H | CF₃ | H | — | — | — |

TABLE 1-continued

Structure (I): a benzene ring with substituents $R^3, R^4, R^5, R^6$ on positions and $R^2, R^1$ on the vinyl/carbonyl group.

Structure (II): a julolidine-type fused ring system with substituents $R^3, R^2, R^1$.

| Compound | Skeleton | $R^1$ | $R^2$ | $R^3$ | $R^4$ | $R^5$ | $R^6$ |
|---|---|---|---|---|---|---|---|
| 31 | II | COOC$_2$H$_5$ | H | H | — | — | — |
| 32 | II | COCH$_3$ | H | H | — | — | — |
| 33 | II | COOC(CH$_3$)$_3$ | H | H | — | — | — |
| 34 | I | H | CH$_3$ | H | —CH$_2$CH$_2$CH$_2$NH— | | H |
| 35 | II | COOH | H | H | — | — | — |
| 36 | I | 4-(COOCH$_3$)-phenyl | H | H | H | OCH$_3$ | H |
| 37 | I | 4-CN-phenyl | H | H | H | OC$_2$H$_5$ | H |
| 38 | I | 4-CN-phenyl | H | H | H | N(C$_8$H$_{17}$)$_2$ | H |
| 39 | I | cyclohexenyl | H | H | H | OH | H |
| 40 | I | 4-Cl-phenyl | H | H | H | NH$_2$ | H |
| 41 | I | 3-Cl-phenyl | H | H | H | NH$_2$ | H |
| 42 | I | 2-Cl-phenyl | H | H | H | NH$_2$ | H |

TABLE 1-continued

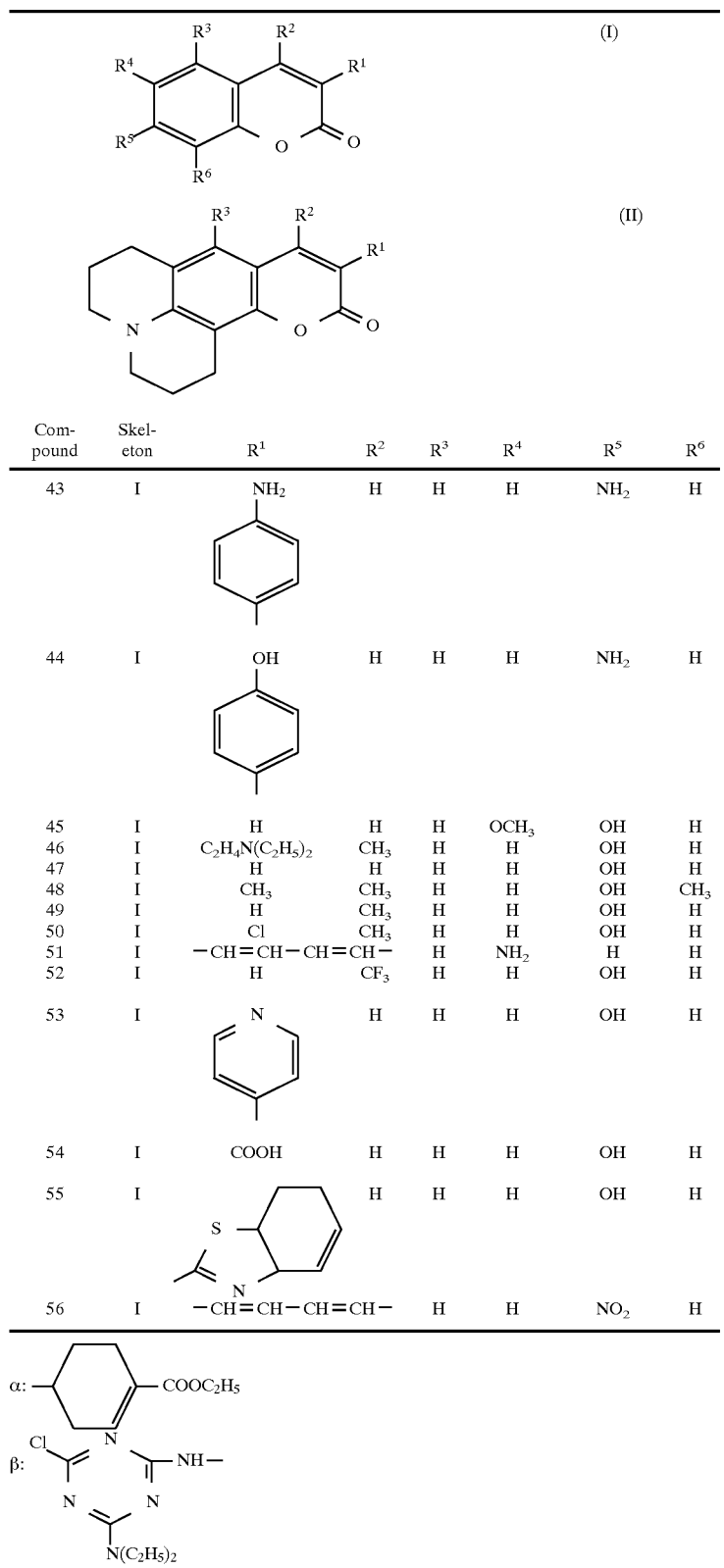

| Compound | Skeleton | R¹ | R² | R³ | R⁴ | R⁵ | R⁶ |
|---|---|---|---|---|---|---|---|
| 43 | I | *p*-NH₂-C₆H₄- | H | H | H | NH₂ | H |
| 44 | I | *p*-OH-C₆H₄- | H | H | H | NH₂ | H |
| 45 | I | H | H | H | OCH₃ | OH | H |
| 46 | I | $C_2H_4N(C_2H_5)_2$ | CH₃ | H | H | OH | H |
| 47 | I | H | H | H | H | OH | H |
| 48 | I | CH₃ | CH₃ | H | H | OH | CH₃ |
| 49 | I | H | CH₃ | H | H | OH | H |
| 50 | I | Cl | CH₃ | H | H | OH | H |
| 51 | I | —CH=CH—CH=CH— | | H | NH₂ | H | H |
| 52 | I | H | CF₃ | H | H | OH | H |
| 53 | I | 4-pyridyl | H | H | H | OH | H |
| 54 | I | COOH | H | H | H | OH | H |
| 55 | I | (benzothiazolyl group) | H | H | H | OH | H |
| 56 | I | —CH=CH—CH=CH— | | H | H | NO₂ | H |

α: cyclohexene-COOC₂H₅ substituent

β: chloro-triazine with NH— and N(C₂H₅)₂ groups

The coumarin derivatives described in Table 1 are known compounds, and are produced, for example by the methods as described in Journal of Japan Chemical Association, 3, 644 (1972); Heterocycles, 7, 933 (177); and Journal of Industrial Chemistry, 71, 1010 (1968). The derivatives may also be commercially available from Eastman Kodak Co., Aldrich Co. and Daito Chemics Co.

The peroxidation-active substance for use in the present invention is a generic term for compounds having a peroxidase activity and includes, for example, peroxidase derived from vegetables, animals or microorganisms (EC. 1. 11.1.7), hemoglobin, heme, iron oxide, iron chloride, sodium iodide, ammonium iodide and molybdate.

Quantitative determination by the method of the present invention is generally carried out in accordance with the manner mentioned below.

The reaction is effected in a mixture (0.005 to 2 mol/liter) of various buffers made from hydrochloric acid, acetic acid, acetate, succinate, nitrate, borate, phthalate, glycine, barbital salt and GOOD and having a pH value of from 2 to 8.

Compound (I) or (II) is employed in an amount of from 0.01 $\mu$mol/liter to 100 mol/liter; hydrogen peroxide in an amount of from 10 $\mu$mol/liter to 100 mmol/liter; the peroxidation-active substance in an amount of from $10^{-9}$ to $2\times10^2$ mg/ml, preferably as a peroxidase in an amount of from $10^{-9}$ to $10^2$ U/ml.

Of the three components, other components than the component to be determined by the method are added to the buffer to prepare a reagent solution; and a sample containing the component to be determined is added to and the reaction is carried at $-10°$ to $90°$ C., preferably from $20°$ to $50°$ C. The total amount of the light as emitted by the reaction solution or the amount of the light for a predetermined period of time is determined with a luminometer or the like in a wavelength range of from 190 to 730 nm. From the determined amount, the amount of the component to be determined in the sample may be determined, using a calibration curve previously formed from a sample containing a known amount of the component to be determined.

Since the amount of the emitted light corresponds to the amount of the component to be determined, the amount of the component may be determined from the integrated amount of the emitted light as determined at the end of the reaction. In general, the amount of the component to be determined may be calculated from the integrated amount of the emitted light for a determined period of time.

Where the component to be determined is an enzyme activity, the enzyme activity may be determined by determining the change in the amount of the emitted light per the unit time.

In carrying out the method of the present invention, a surfactant (for example, Triton X-100, product of Yoneyama Chemical Industry Co.) may optionally be added, if desired, to the reaction solution in an amount of from 0.01 to 5% by weight, so as to prevent the reaction solution from becoming turbid.

In order to enhance the light intensity from the luminous compound used, proteins, polyalkyl-quaternary amines, fluorescent agents, dimethylsulfoxide and the like may optionally be added, if desired, to the reaction solution. In addition, an alkali solution may also be added thereto, if desired. As the protein, mention may be made of bovine serum albumin (BSA), human serum albumin (HSA), human immunoglobulin and egg white albumin; as the polyalkyl-quaternary amine, mention may be made of poly-diaryldimethylammonium chloride and poly[vinylbenzyl (benzyldimethyl-ammonium chloride)]; and as the fluorescent agent, mention may be made of peptide-bond products of fluorescein, 4-fluoro-7-nitrobenzofurazane or 7-fluoro-4-nitrobenzoxadiazole with an amine, amino acid, peptide or protein, or their derivatives. As the alkaline solution, mention may be made of an aqueous solution of sodium hydroxide or potassium hydroxide. The light emission enhancing agents are incorporated to the reaction solution in an amount of from 0.0001 to 10% by weight of the solution.

Hydrogen peroxide which may be quantitatively determined by the present invention is not only hydrogen peroxide as dissolved in a sample but also hydrogen peroxide to be quantitatively produced by an enzymatic reaction.

The peroxidation-active substance capable of being quantitatively determined by the present invention refers to any of the above-mentioned peroxidation-active substances.

The present invention may be applied to determination of hydrogen peroxide or a peroxidase activity which has heretofore been effected for the diagnostic purposes.

Heretofore, for instance, quantitative determination of a substrate has been effected by quantitatively determining hydrogen peroxide stoichiometrically produced from the substrate in a body sample, by use of an enzyme.

Quantitative determination of the enzyme activity in a body sample has also been effected by adding a suitable enzyme or substrate to the sample to cause an enzymatic reaction involving the enzyme or substrate to form hydrogen peroxide whereupon the rate of forming the hydrogen peroxide during the reaction is determined so as to quantitatively determine the enzyme activity in the sample.

As the examples of the substrate or enzyme activity, mentioned are quantitative determination of a substrate to be reacted with a specific oxidase (for example, glucose oxidase, galactose oxidase, cholesterol oxidase, uricase) and determination of the activity of an enzyme such as monoamine oxidase or choline esterase.

A peroxidase is employed as a labeling substance in quantitative determination of an antigen-antibody reaction by means of enzyme immunoassay (EIA), in which the peroxidase activity after the antigen-antibody reaction or the amount of hydrogen peroxide as formed by the action of the peroxidase is quantitatively determined. For instance, mentioned are various methods described in Enzyme Immunoassay (written by Eiji Ishikawa et al., 1987, published by Igaku Shoin Co.). For example, an antigen is reacted with an immobilized antibody and an antibody as labeled with an enzyme such as peroxidase or glucose oxidase, is reacted with the antigen, whereupon the enzyme activity itself or hydrogen peroxide as formed by the action of the enzyme is quantitatively determined. The present invention may be applied in the EIA, whereby drugs or hormones to be contained in a serum or urine as well as a minor component in a body sample, such as carcinoembryonic antigen (CEA), $\alpha$-fetoprotein (AFP) or prostatic acid phosphatase (PAP) is determined.

The present invention is applied to the determination of hydrogen peroxide or the peroxidase activity as exemplified above, whereby a trace amount of a component may be quantitatively determined.

Using Compound (I) or (II) as a labeling substance according to the present invention, antigen-antibody reactions are conducted whereby an antigen or antibody may be quantitatively determined by determining the amount of the emitted light or the light intensity from the antigen-antibody reaction product.

In addition, the present invention may also be applied to a method of determining a polynucleotide.

As the method of determining a polynucleotide, mention may be made of a method in which a polynucleotide which is complementary to the polynucleotide to be determined is labeled with an enzyme such as peroxidase or glucose oxidase or with Compound (I) or (II) and the enzyme activity of the enzyme-labeled polynucleotide as complementary to the polynucleotide to be determined is measured or the labeling Compound (I) or (II) is quantitatively determined so as to determine the amount of the polynucleotide to be determined. The method is described in, for example, "DNA Probes" (published by Jisk Co., 1988), and "DNA Probes II" (published by Jisk Co., 1990).

The characteristic of the present invention of employing the coumarin derivatives represented by formula (I) or (II) is such that the pH range of yielding emission of light is broad, for example, from pH 1 to pH 10 and that a strong light is emitted in an acidic to neutral range for from pH 5 to pH 7. Luminol, isoluminol, lucigenin, acridinium esters and the like which have heretofore been employed could yield emission of light of a satisfactory amount only under a strong alkaline condition. Therefore, using such conventional reagents, detection of substances with an enzyme having an optimum pH range, which is lower than a neutral pH value, for example, peroxidase or the like, is difficult. In accordance with the method of the present invention, employment of even an enzyme having an optimum pH range, which is lower than a neutral pH value, is possible for determination of a substance, under the optimum pH range of the enzyme. In accordance with the present invention, employment of an oxidase, which has an optimum pH value falling within an acidic range and which could not be employed in a conventional determination method by use of a known luminous substance such as luminol or the like, is possible. Therefore, in accordance with the method of the present invention, when determining the activity of the enzyme having the above-mentioned property, the determination may be effected in the range having the maximum activity of the enzyme so that an amount of the enzyme smaller than that detectable by an conventional method may well can be detected.

Legend

—○— Compound 1

—●— Compound 5

- - □ - - Compound 9

- - X - - Luminol

Figure 2:
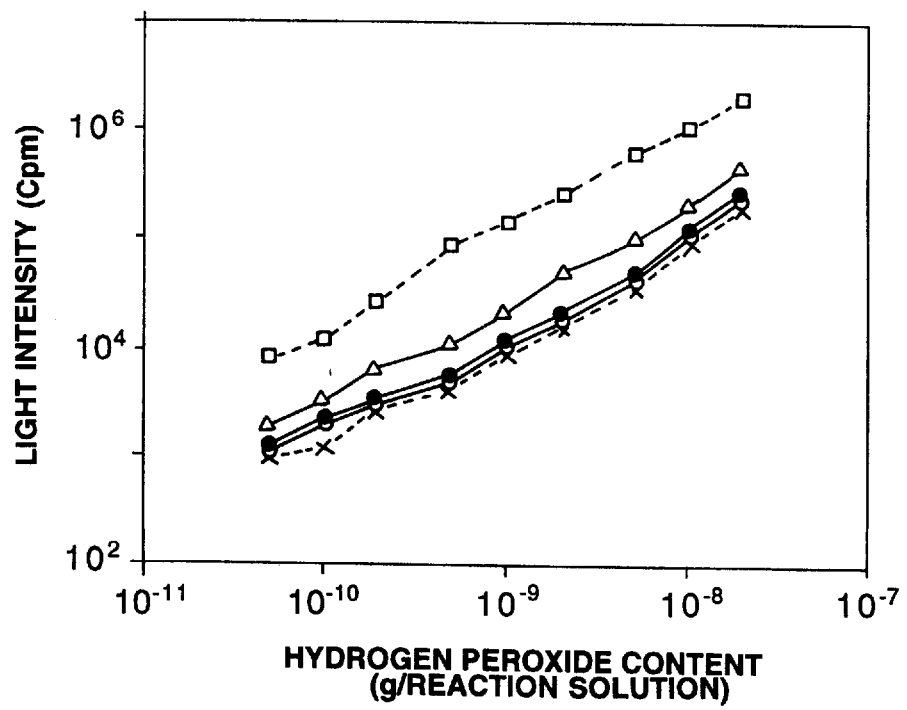

FIG. 2 shows the light intensity of Compounds 10, 12, 14 and 23 and luminol, when a varying concentration of hydrogen peroxide was used.

Legend

—●— Compound 10

- - □ - - Compound 12

—△— Compound 14

—○— Compound 23

- - X - - Luminol

Figure 3:
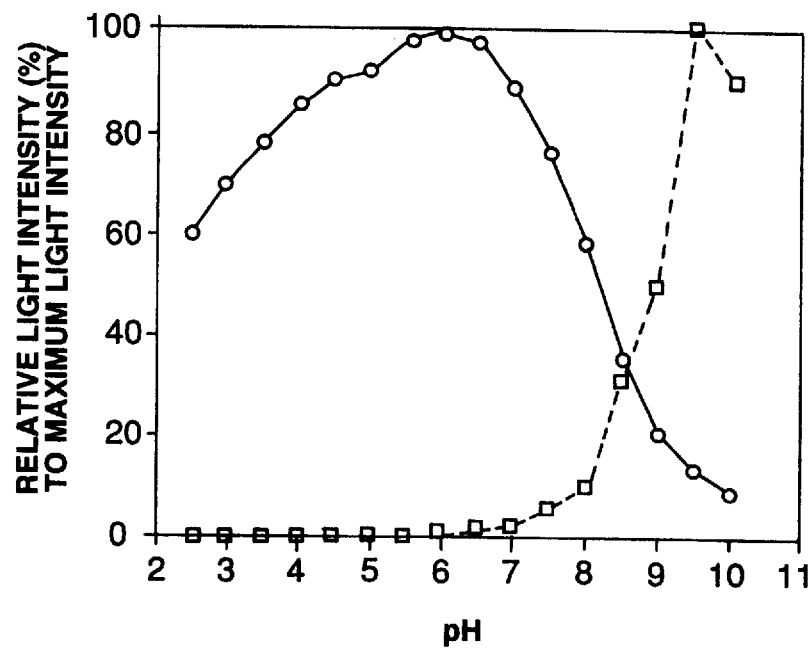

FIG. 3 shows the light intensity of Compound 1 and luminol at a varying pH value.

Legend

—○— Compound 1

- - □ - - Luminol

Figure 4:
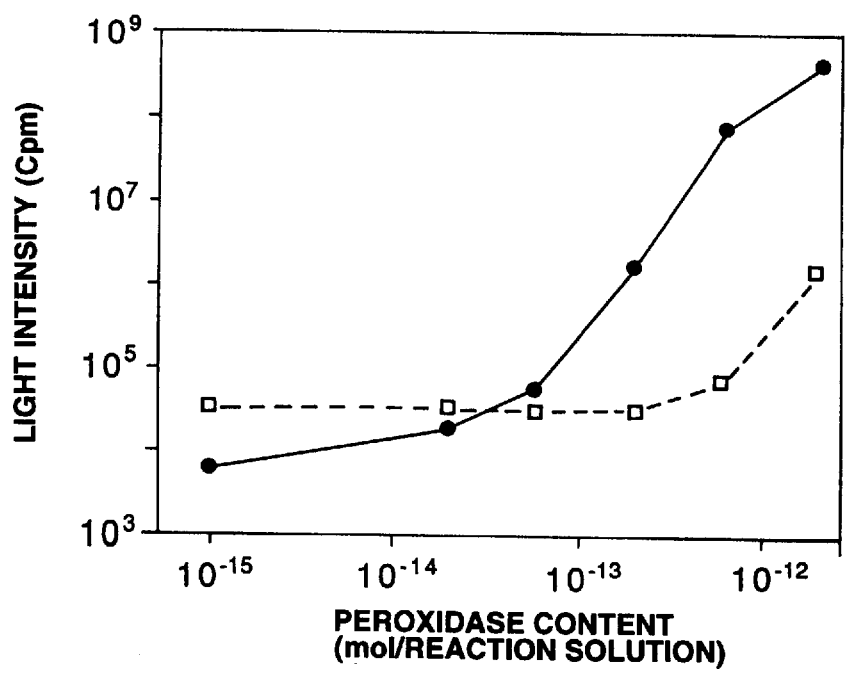

FIG. 4 shows the light intensity of Compound 1 and luminol when a varying concentration of peroxidase was used.

Legend

—●— Compound 1

- - □ - - Luminol

Figure 5:
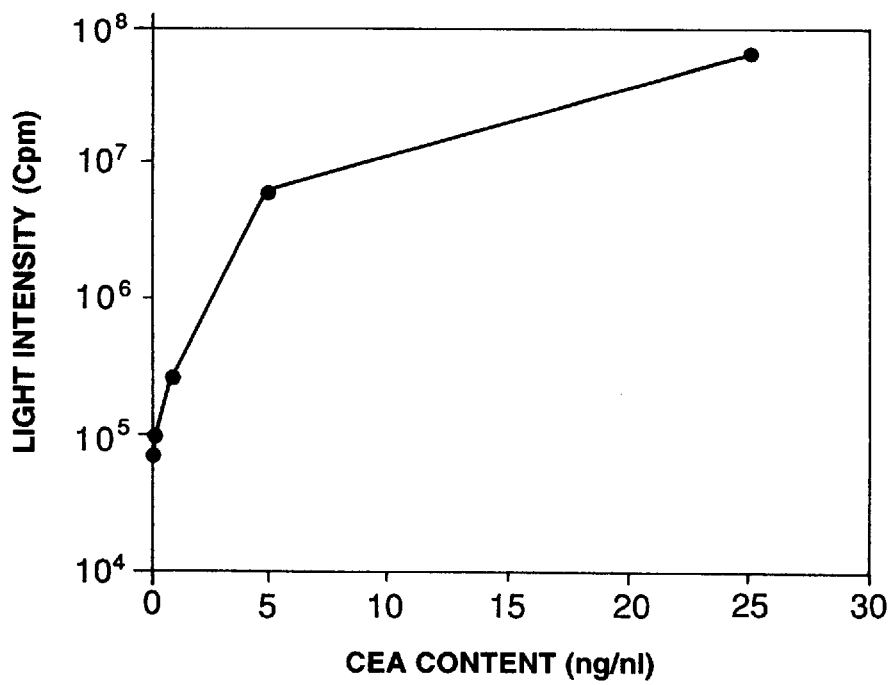

FIG. 5 shows the light intensity of Compound 1, when a varying concentration of CEA was used.

Legend

—●— Compound 1

Figure 6:
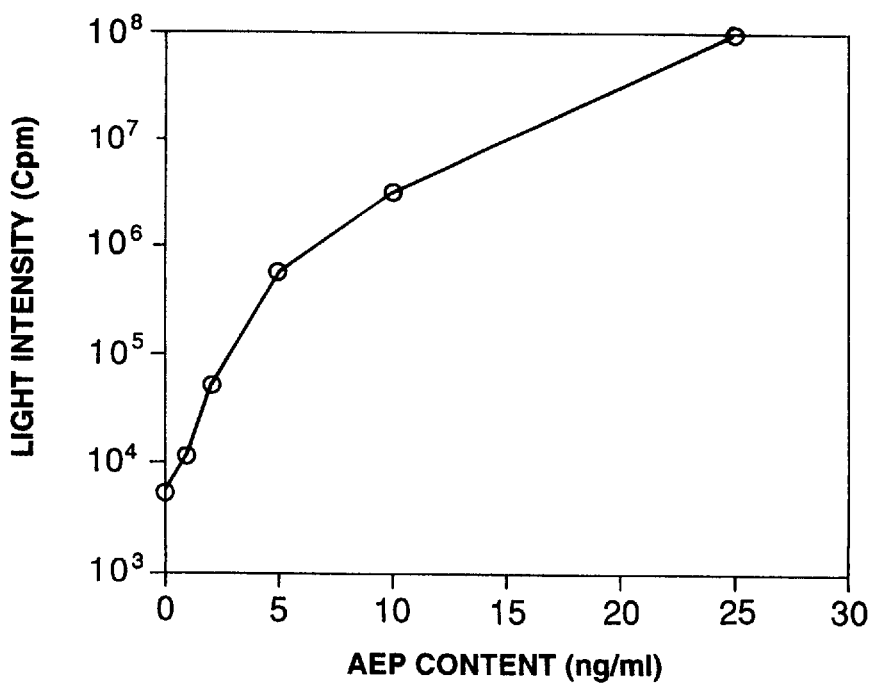

FIG. 6 shows the light intensity of Compound 35, when a varying concentration of AFP was used.

Legend

—○— Compound 35

Figure 7:
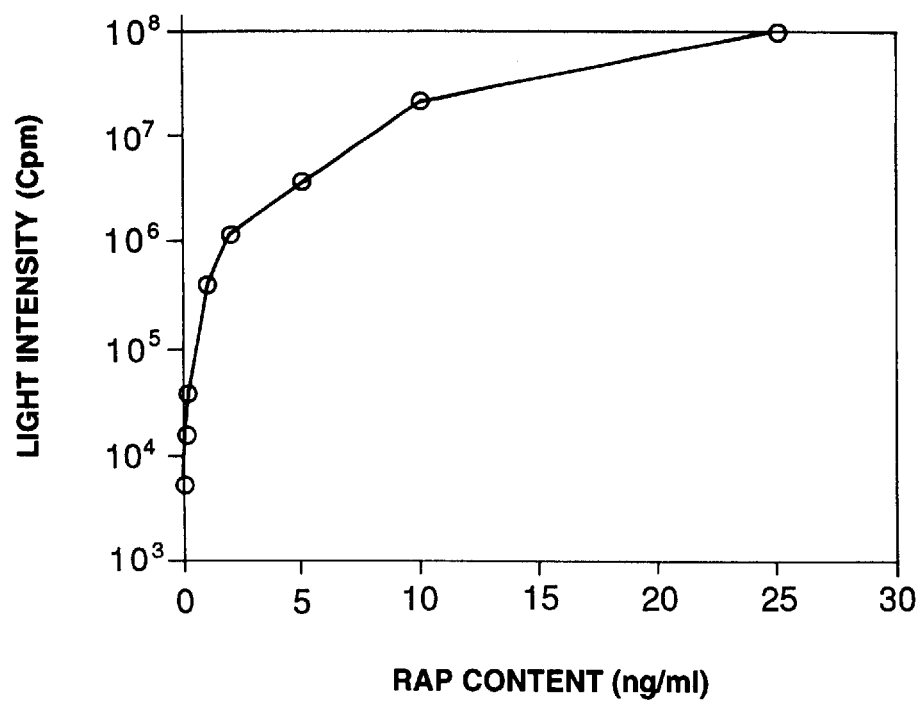

FIG. 7 shows the light intensity of Compound 35, when a varying concentration of PAP was used.

Legend

—○— Compound 35

Figure 8:
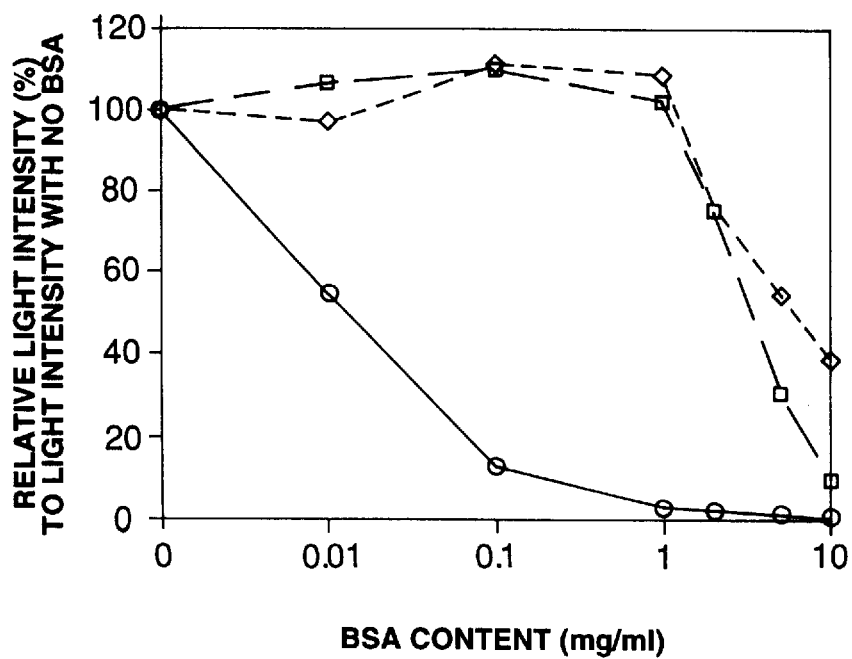

FIG. 8 shows a ratio of the light intensity of Compounds 31 and 35 and acridinium ester (Acridinium-I, product of Dojin Chemical Laboratories Co.) in the presence of a varying concentration of BSA to that in the absence of BSA.

Legend

—□— Compound 31

—◇— Compound 35

—○— Acridinium Ester

BEST MODES OF CARRYING OUT THE INVENTION

Examples of the present invention are mentioned below.

EXAMPLE 1

(Chemiluminescence of Coumarin Derivatives by Peroxidase Reaction)

100 U of a horseradish-derived peroxidase (product of Toyobo Co., Ltd.—the same shall apply hereunder), 50 mg of Triton X-100 and 10 mg of the coumarin derivative of the reference compound luminol (product of Tokyo Chemical Co.—the same shall apply hereunder) as described in Table 2 were dissolved in 100 ml of 20 mmol phosphate buffer (pH 6.0) to prepare a reagent solution.

400 $\mu$l to the reagent solution was put in a test tube and allowed to stand at 37° C. for 10 minutes. Then, the test tube was mounted on a luminometer (Lumicounter 1000; manufactured by Nichion Irika Kikai Seisakusho Co.—the same shall apply hereunder), which had been kept under a constant temperature of 37° C. 10 $\mu$l of 3 mmol/liter of hydrogen peroxide and 10 $\mu$l of 1N sodium hydroxide aqueous solution were added to the reagent solution, whereupon the integrated amount of the emitted light [light intensity (cpm)] from the reaction solution for one minute was determined. The results are shown in Table 2.

TABLE 2

| Compound | Light Intensity (cpm) |
|---|---|
| Luminol | 56314 |
| 1 | 17686759 |
| 2 | 145580 |
| 3 | 184967 |
| 4 | 412709 |
| 5 | 1833121 |
| 6 | 128488 |
| 7 | 112293 |
| 8 | 131044 |

TABLE 2-continued

| Compound | Light Intensity (cpm) |
|---|---|
| 9 | 1935827 |
| 10 | 770399 |
| 11 | 502900 |
| 12 | 2052723 |
| 13 | 525408 |
| 14 | 1210633 |
| 15 | 406754 |
| 16 | 116866 |
| 17 | 330955 |
| 18 | 229856 |
| 19 | 199324 |
| 20 | 134812 |
| 21 | 238450 |
| 22 | 150809 |
| 23 | 769198 |
| 25 | 132540 |
| 31 | 91523 |
| 32 | 263581 |
| 33 | 143003 |
| 35 | 111312 |
| 37 | 79451 |
| 42 | 88021 |
| 46 | 280590 |
| 47 | 62538 |
| 49 | 58321 |
| 50 | 91720 |
| 51 | 132951 |
| 52 | 59253 |
| 53 | 63520 |
| 54 | 86297 |
| 55 | 66534 |
| 56 | 57235 |

Table 2 indicates that the coumarin derivatives as employed in this example produced a light intensity equivalent or superior to that by luminol by reaction with peroxidase in the presence of hydrogen peroxide at pH 6.0.

EXAMPLE 2

(Quantitative Determination of Hydrogen Peroxide)

100 U of peroxidase, 50 mg of Triton X-100 and 10 mg of each of Compounds 1, 5, 9, 10, 12, 14 and 23 and a reference compound luminol were dissolved in 100 ml of 20 mmol phosphate buffer (pH 6.0) to prepare a reagent solution.

400 μl of the reagent solution was put in a test tube and allowed to stand at 37° C. for 10 minutes. Then, the test tube was mounted on a luminometer, which had been kept under a constant temperature of 37° C., and 10 μl of hydrogen peroxide of a different concentration varying within the range of from $5 \times 10^{-11}$ to $2 \times 10^{-8}$ g/(reaction solution) and 10 μl of 1N sodium hydroxide aqueous solution were added to the reaction solution, whereupon the integrated amount of the emitted light from the reaction solution for one minute was determined. The results are shown in FIGS. 1 and 2.

Figure 1:
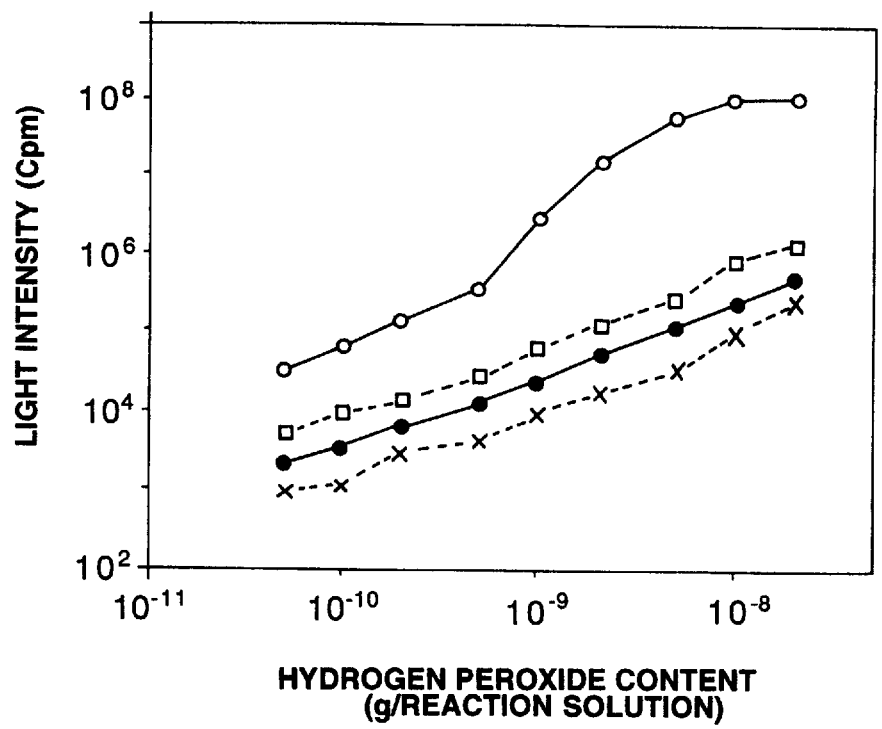
FIG. 1 shows the light intensity of Compounds 1, 5 and 9 and luminol, when a varying concentration of hydrogen peroxide was used.

FIGS. 1 and 2 indicate that the coumarin derivatives as employed herein produced a light intensity equivalent or superior to that by luminol.

EXAMPLE 3

(Light Intensity by Chemiluminescence of Coumarin Derivatives by Peroxidase Reaction Under Varying pH Conditions)

100 U of peroxidase, 50 mg of Triton X-100 and 10 mg of each of Compound 1 and reference compound luminol were dissolved in 100 ml of 20 mmol phthalate buffer (pH 2.5 to 5.5), 20 mmol phosphate buffer (pH 5.5 to 8.0) or 20 mmol borate buffer (pH 8.0 to 10) to prepare a reagent solution.

400 μl of the reagent solution was put in a test tube and allowed to stand at 37° C. for 10 minutes. Then, the test tube was mounted on a luminometer, which had been kept under a constant temperature of 37° C., and 10 μl of 3 mmol/liter of hydrogen peroxide was added to the reagent solution, whereupon the integrated amount of the emitted light from the reaction solution for one minute was determined. FIG. 3 indicates a relative amount with respect of the light emitted from the reaction solution at a varying pH value, defining the maximum amount of the emitted light as 100.

FIG. 3 indicates the optimum light-emitting pH value for Compound 1 is in the acidic range. The light-emitting pH range is much broader than that of luminol.

EXAMPLE 4

(Determination of Peroxidase Activity)

50 mg of Triton X-100 and 10 mg of Compound 1 or a reference compound luminol each were dissolved in 100 ml of 20 mmol phosphate buffer (pH 6.0) to prepare reagent solution 1. As a control, 50 mg of Triton X-100 and 10 mg of luminol were dissolved in 100 ml of 100 mmol borate buffer (pH 9.5) to prepare reagent solution 2. 400 μl of the reagent solution 1 or 2 was put in a test tube and allowed to stand at 37° C. for 10 minutes. Then, the test tube was mounted on a luminometer which had been kept under a constant temperature of 37° C., and 10 μl of 300 mmol/liter of hydrogen peroxide and 10 μl of a varying concentration of a peroxidase solution were added to the reagent solution, whereupon the integrated amount of the emitted light from the reaction solution for one minute was determined. The results are shown in FIG. 4.

FIG. 4 indicates that a calibration curve of peroxidase activity was obtained by the use of a lower concentration of Compound 1 than that of luminol.

EXAMPLE 5

[Quantitative Determination of Carcinoembryonic Antigen (CEA)]

(1) Labeling of rabbit anti-human CEA antibody with glucose oxidase (GOD)

Labeling of anti-CEA antibody with GOD was carried out according to the method of Ishikawa et al (Enzyme Immunoassay, p. 82; by Eiji Ishikawa et al., 1987, published by Igaku Shoin Co.). That is, using N-succinimidyl-4-(N-maleimidomethyl)cyclohexane-1-carboxylate (produced by Pierce Co.), maleimido group was introduced into GOD. Separately, F(ab')₂ fragment as obtained by digestion of anti-CEA antibody with pepsin was reduced to obtain F(ab') containing no SH group. The resulting GOD and F(ab') were mixed with each other to obtain a GOD-labeled anti-CEA antibody.

(2) Preparation of anti-CEA antibody-fixed magnetic grains

As the magnetic grains for fixation of anti-CEA antibody Magnosphere (trade name of Sterogene Bioseparation Co.— the same shall apply hereunder) was used. A solution of anti-CEA antibody in 0.1 mol phosphate buffer (pH 7.0) was added to the same amount of the magnetic grains. A coupling reagent of sodium borohydride was added thereto in a final concentration of 0.1 mol and the mixture was stirred for 2 hours. The grains were collected with a magnet, the supernatant was removed by suction, and 500 μl of a phosphate buffer containing 0.1% BSA and 0.1% NaN$_3$ was added to the collected magnetic grains to obtain anti-CEA antibody-fixed magnetic grains.

(3) Quantitative determination of CEA

100 U of peroxidase, 50 mg of Triton X-100 and 10 mg of Compound 1 were dissolved in 100 ml of 20 mmol phosphate buffer (pH 6.0) to prepare a reagent solution. 400 μl of the reagent solution was put in a test tube and was allowed to stand at 37° C. for 10 minutes. Then, the test tube was mounted on a luminometer which had been kept under a constant temperature of 37° C. Separately, 50 μl of a varying concentration of standard CEA, and 100 μl of the anti-CEA antibody-fixed magnetic grains and 100 μl of GOD-labeled anti-CEA antibody were mixed with each other and the mixture was allowed to stand for one hour at 37° C., whereby CEA was bound to the GOD-labeled anti-CEA antibody and to the anti-CEA antibody-fixed magnetic grains. The grains were collected with a magnet, the supernatant was removed by suction, and 100 μl of a solution containing 54 mg/ml glucose in 10 mmol citrate buffer (pH 5.0) as a substrate for the CEA-bound GOD was added to the collected magnetic grains and the mixture was allowed to stand for 30 minutes at 37° C. 100 ml of 50 mmol glycine buffer (pH 11.0) was added thereto as a reaction-stopping solution. The grains were removed with a magnet, and 10 μl of the supernatant was added to the reagent solution. The reaction mixture-containinig test tube was mounted on a luminometer, whereupon the integrated amount of the emitted light from the reaction solution for one minute was determined. The results are shown in FIG. 5.

EXAMPLE 6

(Chemiluminescence of Coumarin Derivatives by Peroxidase Reaction)

100 U of peroxidase, 50 mg of Triton X-100 and 10 mg of each of the coumarin derivatives or reference compound luminol as described in Table 3 were dissolved in 100 ml of 20 mmol of acetate buffer (pH 4.0) to prepare a reagent resolution.

400 μl of the reagent solution was put in a test tube and allowed to stand at 37° C. for 10 minutes. Then, the test tube was mounted on a luminometer which had been kept under a constant temperature of 37° C. 10 μl of 3 mmol/liter of hydrogen peroxide and 10 μl of 1N sodium hydroxide solution were added thereto, whereupon the integrated amount of the emitted light from the reaction solution for one minute was determined. The results are shown in Table 3.

TABLE 3

| Compound | Light Intensity (cpm) |
|---|---|
| Luminol | 4721 |
| 1 | 1734530 |
| 2 | 62305 |
| 7 | 33414 |
| 8 | 28231 |
| 23 | 3806713 |
| 24 | 92518 |
| 26 | 58057 |
| 29 | 34004 |
| 30 | 349566 |
| 31 | 1552199 |
| 32 | 781520 |
| 33 | 1349215 |
| 34 | 12618 |
| 35 | 362587 |
| 38 | 11353 |
| 40 | 24831 |
| 41 | 31522 |
| 42 | 135090 |
| 43 | 24442 |
| 44 | 12418 |
| 56 | 97516 |

Table 3 indicates that the coumarin derivatives as employed in this example produced a light intensity much higher than that by the reaction of luminol with hydrogen peroxide in the presence of peroxidase even under an acidic condition of pH 4.0.

EXAMPLE 7

(Quantitative Determination of Coumarin Derivative)

100 U of peroxidase, 50 mg of Triton X-100 and a predetermined concentration of the coumarin derivative as described in Table 4 were dissolved in 100 ml of 20 mmol acetate buffer (pH 4.0) or 20 mmol phosphate buffer (pH 6.0) to prepare a reagent solution.

400 μl of the reagent solution was put in a test tube and allowed to stand at 37° C. for 10 minutes. Then, the test tube was mounted on a luminometer which had been kept under a constant temperature of 37° C., and 10 μl of 3 mmol/liter of hydrogen peroxide was added to the reagent solution, whereupon the integrated amount of the emitted light from the reaction solution for one minute was determined. The results are shown in Table 4.

TABLE 4

| Compound | pH | Concentration of Coumarin Derivatives in Reagent Solution (mg/ml) | | | | | | |
|---|---|---|---|---|---|---|---|---|
| | | $10^{-2}$ | $10^{-3}$ | $10^{-4}$ | $10^{-5}$ | $10^{-6}$ | $10^{-7}$ | $10^{-8}$ |
| 1 | 6 | $1.23 \times 10^7$ | $8.67 \times 10^6$ | $3.46 \times 10^4$ | — | | | |
| 2 | 6 | $1.36 \times 10^5$ | $9.26 \times 10^4$ | $1.52 \times 10^2$ | — | | | |
| 3 | 6 | $1.22 \times 10^5$ | $7.35 \times 10^4$ | $1.59 \times 10^2$ | — | | | |
| 4 | 6 | $5.38 \times 10^5$ | $1.96 \times 10^5$ | $3.24 \times 10^3$ | $1.11 \times 10^2$ | — | | |
| 5 | 6 | $2.46 \times 10^6$ | $1.05 \times 10^5$ | $7.24 \times 10^4$ | $2.32 \times 10^2$ | — | | |
| 6 | 6 | $1.59 \times 10^5$ | $8.42 \times 10^4$ | $1.69 \times 10^2$ | — | | | |
| 7 | 6 | $1.10 \times 10^5$ | $6.38 \times 10^4$ | $2.03 \times 10^2$ | — | | | |
| 8 | 6 | $3.11 \times 10^8$ | $1.52 \times 10^5$ | $7.49 \times 10^4$ | $3.26 \times 10^3$ | — | | |

TABLE 4-continued

| Compound | pH | Concentration of Coumarin Derivatives in Reagent Solution (mg/ml) | | | | | | |
|---|---|---|---|---|---|---|---|---|
| | | $10^{-2}$ | $10^{-3}$ | $10^{-4}$ | $10^{-5}$ | $10^{-6}$ | $10^{-7}$ | $10^{-8}$ |
| 9 | 6 | $2.22 \times 10^5$ | $9.32 \times 10^5$ | $6.42 \times 10^4$ | $2.14 \times 10^3$ | — | | |
| 10 | 6 | $7.14 \times 10^5$ | $2.04 \times 10^5$ | $4.32 \times 10^4$ | — | | | |
| 11 | 6 | $5.54 \times 10^5$ | $1.02 \times 10^5$ | $3.93 \times 10^4$ | — | | | |
| 12 | 6 | $2.83 \times 10^8$ | $1.08 \times 10^5$ | $5.11 \times 10^4$ | $2.98 \times 10^3$ | — | | |
| 13 | 6 | $4.90 \times 10^5$ | $1.30 \times 10^5$ | $3.11 \times 10^4$ | — | | | |
| 14 | 6 | $1.55 \times 10^8$ | $8.00 \times 10^5$ | $4.39 \times 10^4$ | — | | | |
| 15 | 6 | $3.16 \times 10^5$ | $1.00 \times 10^5$ | $2.69 \times 10^4$ | — | | | |
| 16 | 6 | $9.00 \times 10^4$ | $5.18 \times 10^4$ | $1.33 \times 10^3$ | — | | | |
| 17 | 6 | $3.30 \times 10^5$ | $2.90 \times 10^4$ | $3.10 \times 10^3$ | — | | | |
| 18 | 6 | $2.77 \times 10^5$ | $3.21 \times 10^4$ | $2.56 \times 10^3$ | — | | | |
| 19 | 6 | $2.63 \times 10^5$ | $4.80 \times 10^4$ | $1.89 \times 10^3$ | — | | | |
| 20 | 6 | $1.16 \times 10^5$ | $7.74 \times 10^4$ | $5.86 \times 10^3$ | — | | | |
| 21 | 6 | $2.64 \times 10^5$ | $1.60 \times 10^4$ | $4.00 \times 10^3$ | — | | | |
| 22 | 6 | $1.08 \times 10^5$ | $8.39 \times 10^4$ | $6.21 \times 10^3$ | — | | | |
| 23 | 4 | $8.00 \times 10^5$ | $2.60 \times 10^5$ | $8.14 \times 10^4$ | $6.30 \times 10^3$ | $1.50 \times 10^3$ | — | |
| 24 | 4 | $1.00 \times 10^5$ | $6.30 \times 10^4$ | $7.88 \times 10^3$ | — | | | |
| 25 | 6 | $1.50 \times 10^5$ | $8.41 \times 10^4$ | $5.30 \times 10^3$ | — | | | |
| 26 | 4 | $6.20 \times 10^4$ | $3.14 \times 10^3$ | $1.00 \times 10^3$ | — | | | |
| 29 | 4 | $3.11 \times 10^4$ | $2.71 \times 10^3$ | $1.64 \times 10^3$ | — | | | |
| 30 | 4 | $4.84 \times 10^5$ | $6.92 \times 10^4$ | $4.30 \times 10^3$ | — | | | |
| 31 | 4 | $1.13 \times 10^8$ | $1.10 \times 10^8$ | $9.00 \times 10^4$ | $3.80 \times 10^3$ | $2.37 \times 10^3$ | $1.02 \times 10^3$ | $8.20 \times 10^2$ |
| 32 | 4 | $6.93 \times 10^5$ | $5.11 \times 10^5$ | $4.62 \times 10^4$ | $1.90 \times 10^3$ | — | | |
| 33 | 4 | $1.10 \times 10^8$ | $9.00 \times 10^5$ | $8.32 \times 10^4$ | $1.20 \times 10^3$ | — | | |
| 34 | 4 | $1.21 \times 10^4$ | $8.30 \times 10^3$ | $4.18 \times 10^3$ | — | | | |
| 35 | 4 | $3.60 \times 10^5$ | $2.50 \times 10^5$ | $9.00 \times 10^4$ | $9.30 \times 10^3$ | $2.30 \times 10^3$ | $1.11 \times 10^3$ | $7.00 \times 10^2$ |
| 37 | 6 | $8.05 \times 10^4$ | $2.43 \times 10^4$ | $8.87 \times 10^3$ | — | | | |
| 38 | 4 | $1.36 \times 10^4$ | $7.28 \times 10^3$ | $1.00 \times 10^3$ | — | | | |
| 40 | 4 | $2.00 \times 10^4$ | $6.71 \times 10^3$ | $4.40 \times 10^3$ | — | | | |
| 41 | 4 | $3.59 \times 10^4$ | $5.00 \times 10^3$ | $1.92 \times 10^3$ | — | | | |
| 42 | 4 | $1.51 \times 10^5$ | $8.11 \times 10^4$ | $6.50 \times 10^3$ | $1.00 \times 10^3$ | — | | |
| 43 | 4 | $2.10 \times 10^4$ | $6.18 \times 10^3$ | $2.00 \times 10^3$ | — | | | |
| 44 | 4 | $1.06 \times 10^4$ | $7.60 \times 10^3$ | $1.03 \times 10^3$ | — | | | |
| 46 | 6 | $2.74 \times 10^5$ | $9.18 \times 10^4$ | $1.27 \times 10^4$ | $6.59 \times 10^3$ | — | | |
| 47 | 6 | $6.25 \times 10^4$ | $1.68 \times 10^4$ | $7.36 \times 10^3$ | $2.50 \times 10^3$ | — | | |
| 49 | 6 | $5.11 \times 10^4$ | $2.41 \times 10^4$ | $1.81 \times 10^4$ | $5.63 \times 10^3$ | — | | |
| 50 | 6 | $1.18 \times 10^5$ | $7.33 \times 10^4$ | $5.40 \times 10^3$ | $1.00 \times 10^3$ | — | | |
| 51 | 6 | $1.29 \times 10^5$ | $6.10 \times 10^4$ | $4.18 \times 10^3$ | — | | | |
| 52 | 6 | $6.11 \times 10^4$ | $1.32 \times 10^4$ | $5.91 \times 10^3$ | — | | | |
| 53 | 6 | $7.00 \times 10^4$ | $8.08 \times 10^3$ | $2.16 \times 10^3$ | — | | | |
| 54 | 6 | $8.15 \times 10^4$ | $7.00 \times 10^3$ | $1.13 \times 10^3$ | — | | | |
| 55 | 6 | $5.90 \times 10^4$ | $3.21 \times 10^3$ | $1.00 \times 10^3$ | — | | | |
| 56 | 4 | $1.21 \times 10^5$ | $6.48 \times 10^4$ | $4.69 \times 10^3$ | — | | | |

Note:
1) Not emitted light.
2) The numerals in the table indicate the light intensity (cpm).

Table 4 indicates that Compounds 4, 5, 8, 9, 12, 23, 31, 32, 33, 35, 42, 46, 47, 49 and 50, preferably Compounds 31 and 35 are quantitatively determined by chemiluminescence to the extent of such an extremely low concentration.

EXAMPLE 8

[Quantitative Determination of α-Fetoprotein (AFP)]

(1) Labeling of goat anti-human AFP antibody with Compound 35

Anti-AFP antibody as labeled with Compound 35 was prepared in the manner as mentioned below. Specifically, the carboxyl group in Compound 35 was reacted with the amino group in anti-AFP antibody in the presence of 1-ethyl-3-(3-dimethylaminopropyl)carbodiimide (hereinafter referred to as EDC) at pH 7.0 and bound to each other to obtain a Compound 35-labeled anti-AFP antibody.

(2) Preparation of anti-AFP antibody-fixed magnetic grains

As the magnetic grains for fixation of anti-AFP antibody Magnosphere was used. A solution of anti-AFP antibody in 0.1 mol phosphate buffer (pH 7.0) was added to the same amount of the magnetic grains. A coupling reagent of sodium borohydride was added thereto in a final concentration of 0.1 mol and the mixture was stirred for 2 hours. The grains were collected with a magnet, the supernatant was removed by suction, and 500 μl of a phosphate buffer containing 0.1% BSA and 0.1% $NaN_3$ was added to the collected magnetic grains to obtain anti-AFP antibody-fixed magnetic grains.

(3) Quantitative determination of AFP

100 U of peroxidase and 50 mg of Triton X-100 were dissolved in 100 ml of 20 mmol acetate buffer (pH 4.0) to prepare a reagent solution. Separately, 50 μl of a varying concentration of standard AFP, 100 μl of the anti-AFP antibody-fixed magnetic grains and 100 μl of Compound 35-labeled anti-AFP antibody were mixed with each other and the mixture was allowed to stand for one hour at 37° C., whereby AFP was bound to the Compound 35-labeled anti-AFP antibody and to the anti-AFP antibody-fixed magnetic grains. The grains were collected with a magnet, the supernatant was removed by suction, and the thus collected grains-containing test tube was mounted on a luminometer which had been kept under a constant temperature of 37° C. 400 μl of the reagent solution and 20 μl of 3 mmol/liter hydrogen peroxide, which had previously been kept at 37° C., were added thereto, whereupon the integrated amount of the emitted light from the reaction solution for one minute was determined. The results are shown in FIG. 6.

EXAMPLE 9

(Quantitative Determination of Prostatic Acid Phosphatase (PAP)

(1) Labeling of goat anti-human PAP antibody with Compound 35

Anti-PAP antibody as labeled with Compound 35 was prepared in the manner as mentioned below. Specifically, 50 mg of Compound 35 was dissolved in 10 ml of dioxane, 75 mg of EDC and 50 mg of N-hydroxysuccinic acid imide were added thereto and the mixture was stirred for 24 hours at room temperature, and the reaction solution was concentrated to dryness. The concentrate was extracted with ethyl acetate/water, and the organic layer was concentrated to dryness. The concentrate was again dissolved in 10 ml of dioxane, and 50 mg of β-alanine was added thereto. The mixture was allowed to stand for 4 hours at room temperature. Then, the reaction solution was concentrated to dryness to obtain a solid.

The solid and goat anti-human PAP antibody were mixed with each other in the presence of EDC at pH 7.0 to obtain a Compound 35-labeled anti-PAP antibody.

(2) Preparation of anti-PAP antibody-fixed magnetic grains

As the magnetic grains for fixation of anti-PAP antibody, Magnosphere was used. A solution of anti-PAP antibody in 0.1 mol phosphate buffer (pH 7.0) was added to the same amount of the magnetic grains. A coupling reagent of sodium borohydride was added thereto in a final concentration of 0.1 mol and the mixture was stirred for 2 hours. The grains were collected with a magnet, the supernatant was removed by suction, and 500 μl of a phosphate buffer containing 0.1% BSA and 0.1% NaN$_3$ was added to the collected magnetic grains to obtain anti-PAP antibody-fixed magnetic grains.

(3) Quantitative determination of PAP

100 U of peroxidase and 50 mg of Triton X-100 were dissolved in 100 ml of 20 mmol acetate buffer (pH 4.0) to prepare a reagent solution. Separately, 50 μl of a varying concentration of standard PAP, 100 μl of the anti-PAP antibody-fixed magnetic grains and 100 μl of the Compound 35-labeled anti-PAP antibody were mixed with each other and the mixture was allowed to stand for one hour at 37° C., whereby PAP was bound to the Compound 35-labeled anti-PAP antibody and to the anti-PAP antibody-fixed magnetic grains. The grains were collected with a magnet, the supernatant was removed by suction, and the thus collected grains-containing test tube was mounted on a luminometer, which had been kept under a constant temperature of 37° C. 400 μl of the reagent solution and 20 μl of 3 mmol/liter hydrogen peroxide, which had previously been kept at 37° C., were added thereto, whereupon the integrated amount of the emitted light from the reaction solution for one minute was determined. The results are shown in FIG. 7.

EXAMPLE 10

(Influences by Proteins)

100 U of peroxidase, 50 mg of Triton X-100 and 10 mg of Compound 31 or Compound 35 were dissolved in 100 ml of 20 mmol acetate buffer (pH 4.0) to prepare a reagent solution.

As a control, 50 mg of Triton X-100 and 0.1 mg of acridinium ester (Acridinium-I, product of Dojin Chemical Laboratories Co.) were dissolved in 100 ml of 20 mmol phosphate buffer (pH 6.0) to prepare a reagent solution.

BSA of a predetermined concentration was added to each reagent solution. 400 μl of the reagent solution was put in a test tube and allowed to stand at 37° C. for 10 minutes. Then, the test tube was mounted on a luminometer which had been kept under a constant temperature of 37° C. For the test system containing Compound 31 or Compound 35, 10 μl of 3 mmol/liter hydrogen peroxide was added thereto. For the control system containing acridinium ester, 10 μl of 3 mmol/liter hydrogen peroxide and 10 μl of 1N sodium hydroxide were added thereto. In both systems, the integrated amount of the emitted light from the reaction solution for one minute was determined. The results are shown in FIG. 8.

FIG. 8 indicates that Compound 31 and Compound 35 are much less affected by BSA in the reaction system than acridinium ester.

EFFECT OF THE INVENTION

Due to the chemiluminescence using coumarin derivatives according to the present invention, a trace amount of hydrogen peroxide, a peroxidation-active substance or a coumarin derivative or a trace amount of a substance (e.g., CEA, AFP, PAP), to which a peroxidation-active substance, oxidase or coumarin derivative has been bound by chemical bonding, may be quantitatively determined with almost no influence by proteins in the case where the pH value of the reaction solution is within a neutral to acidic range.

We claim:

1. A method of quantitatively determining one of a peroxidation-active substance, hydrogen peroxide or a coumarin derivative represented by the formula:

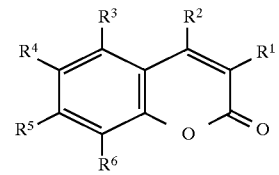

in which $R^1$ represents hydrogen, $C_{1-8}$ linear or branched alkoxy, substituted or unsubstituted phenyl, substituted or unsubstituted naphthyl, cyano, carboxyl, $C_{1-8}$ linear or branched alkoxycarbonyl, $C_{1-8}$ linear or branched alkanoyl, pyridyl or benzothiazolinyl;

$R^2$, $R^3$, $R^4$ and $R^6$ are independently hydrogen or substituted or unsubstituted $C_{1-8}$ linear or branched alkyl; and $R^5$ represents $C_{1-8}$, linear or branched alkoxy, nitro or substituted or unsubstituted amino; or $R^1$ and $R^2$ combined together form $C_{2-4}$ alkylene or $C_{2-4}$ alkenylene; or $R^4$ and $R^5$ combined together form —CH$_2$CH$_2$CH$_2$NH—, the substituted phenyl, naphthyl and alkyl being independently substituted with 1–5 cyano, halogen, amino independently substituted with 0 to 2 $C_{1-8}$ linear or branched alkyl, substituted or unsubstituted heterocyclic group (wherein the heterocyclic group is independently triazinyl, pyrazinyl, pyridyl or pyrimidinyl independently substituted with 0 to 2 cyano, halogen, amino, alkoxy, hydroxy or $C_{1-8}$ linear or branched dialkylamino), $C_{1-8}$ linear or branched alkyl, $C_{1-8}$ linear or branched alkoxy, carboxy, $C_{1-8}$ linear or branched alkoxycarbonyl and hydroxy, and the substituted amino being independently substituted with 1 or 2 $C_{1-8}$ linear or branched alkyl, triazinyl, pyrazinyl, pyridyl or pyrimidinyl; in a sample, comprising the steps of:

(A) selecting a known amount of two substances selected from the peroxidation-active substance, hydrogen peroxide and coumarin derivative or salt thereof;

(B) reacting said two substances with said sample having an unknown amount of the remaining substance from said peroxidation active substance, hydrogen peroxide, or coumarin derivative or salt thereof;

(C) determining the intensity of light emitted from the reacted solution; and (D) comparing the intensity of said emitted light with a calibration curve.

2. A method of quantitatively determining one of a peroxidation-active substance, hydrogen peroxide or a coumarin derivative represented by the formula:

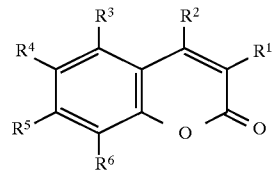

in which $R^1$ represents hydrogen, halogen, $C_{1-8}$ linear or branched alkoxy, substituted or unsubstituted $C_{1-8}$ linear or branched alkyl, substituted or unsubstituted phenyl, substituted or unsubstituted naphthyl, cyano, carboxyl, $C_{1-8}$ linear or branched alkoxycarbonyl, $C_{1-8}$ linear or branched alkanoyl, pyridyl or benzothiazolinyl;

$R^2$, $R^3$, $R^4$ and $R^6$ are independently hydrogen, hydroxy or substituted or unsubstituted $C_{1-8}$ linear or branched alkyl; and $R^5$ represents hydrogen, hydroxy, $C_{1-8}$ linear or branched alkoxy, nitro, substituted or unsubstituted $C_{1-8}$ linear or branched alkyl, substituted or unsubstituted amino, substituted or unsubstituted phenyl, substituted or unsubstituted naphthyl, cyano, carboxyl, $C_{1-8}$ linear or branched alkoxycarbonyl, $C_{1-8}$ linear or branched alkanoyl, pyridyl or benzothiazolinyl; or $R^1$ and $R^2$ combined together form $C_{2-4}$ alkylene or $C_{2-4}$ alkylene or $C_{2-4}$ alkenylene; or $R^4$ and $R^5$ combined together form —$CH_2CH_2CH_2NH$—; the substituted phenyl, naphthyl and alkyl being independently substituted with 1–5 cyano, halogen, amino independently substituted with 0 to 2 $C_{1-8}$ linear or branched alkyl, substituted or unsubstituted heterocyclic group (wherein the heterocyclic group is independently triazinyl, pyrazinyl, pyridyl or pyrimidinyl independently substituted with 0 to 2 cyano, halogen, amino, alkoxy, hydroxy or $C_{1-8}$ linear or branched dialkylamino), $C_{1-8}$ linear or branched alkyl, $C_{1-8}$ linear or branched alkoxy, carboxy, $C_{1-8}$ linear or branched alkoxycarbonyl and hydroxy and the substituted amino being independently substituted with 1 or 2 $C_{1-8}$ linear or branched alkyl, triazinyl, pyrazinyl, pyridyl or pyrimidinyl, with the proviso that when $R^6$ is hydrogen, at least one of $R^1$, $R^2$ and $R^3$ cannot be hydrogen; in a sample, comprising the steps of:

(A) selecting a known amount of two substances selected from the peroxidation-active substance, hydrogen peroxide and coumarin derivative or salt thereof;

(B) reacting said two substances with said sample having an unknown amount of the remaining substance from said peroxidation active substance, hydrogen peroxide, or coumarin derivative or salt thereof;

(C) determining the intensity of light emitted from the reacted solution; and (D) comparing the intensity of said emitted light with a calibration curve.

3. The method according to claim 1 in which $R^1$ is hydrogen, optionally substituted phenyl, optionally substituted naphthyl, pyridyl, benzothiazolinyl or cyano.

4. The method according to claim 2 in which $R^1$ is hydrogen, optionally substituted phenyl, optionally substituted naphthyl, pyridyl, benzothiazolinyl or cyano.

5. The method according to claim 1, wherein $R^1$ is

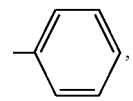

$R^2$–$R^4$ and $R^6$ are all H, and $R^5$ is —$NH_2$.

6. The method according to claim 1, wherein $R^1$, $R^3$, $R^4$ and $R^6$ are all H, $R^2$ is —$CH_3$, and $R^5$ is —$NH_2$.

7. The method according to claim 1, wherein $R^1$ is

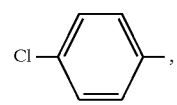

$R^2$–$R^4$ and $R^6$ are all H, and $R^5$ is —$N(C_2H_5)_2$.

8. The method according to claim 1, wherein $R^1$ is

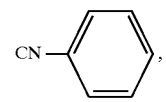

$R^2$–$R^4$ and $R^6$ are all H, and $R^5$ is —$N(C_2H_5)_2$.

9. The method according to claim 1, wherein $R^1$, $R^3$, $R^4$ and $R^6$ are all H, $R^2$ is —$CH_3$, and $R^5$ is —$N(C_2H_5)_2$.

10. The method according to claim 1, wherein $R^1$ is

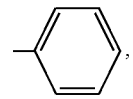

$R^2$ is —$CH_3$, $R^3$, $R^4$ and $R^6$ are all H and $R^5$ is —$N(C_2H_5)_2$.

11. The method according to claim 1, wherein $R^1$ is —CN, $R^2$–$R^4$ and $R^6$ are all H, and $R^5$ is —$NO_2$.

12. The method according to claim 1, wherein $R^1$ is

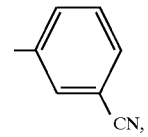

$R^2$–$R^4$ and $R^6$ are all H, and $R^5$ is —$OCH_3$.

13. The method according to claim 1, wherein $R^1$, $R^3$ and $R^6$ are all H, $R^2$ and $R^4$ are —$CH_3$, and $R^5$ is —$NHC_2H_5$.

14. The method according to claim 1, wherein $R^1$ is

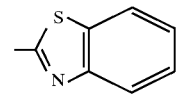

$R^2$–$R^4$ and $R^6$ are all H, and $R^5$ is —$N(C_2H_5)_2$.

15. The method according to claim 1, wherein $R^1$, $R^3$, $R^4$ and $R^6$ are all H, $R^2$ is —$CF_3$ and $R^5$ is —$N(CH_3)_2$.

16. The method according to claim 1, wherein $R^1$, $R^3$ and $R^6$ are all H, $R^2$ is —$CH_3$, and $R^4$ and $R^5$ together form —$CH_2CH_2CH_2NH$—.

17. The method according to claim 1, wherein $R^1$ is

—⟨phenyl⟩—CN, $R^2$–$R^4$ and $R^6$ are all H, and $R^5$ is $N(C_8H_{17})_2$.

18. The method according to claim 1, wherein $R^1$ is

—⟨phenyl⟩—Cl, $R^2$–$R^4$ and $R^6$ are all H, and $R^5$ is —$NH_2$.

19. The method according to claim 1, wherein $R^1$ is

—⟨phenyl with Cl at meta⟩, $R^2$–$R^4$ and $R^6$ are all H, and $R^5$ is —$NH_2$.

20. The method according to claim 1, wherein $R^1$ is

—⟨phenyl with Cl⟩, $R^2$–$R^4$ and $R^6$ are all H, and $R^5$ is —$NH_2$.

21. The method according to claim 1, wherein $R^1$ is

—⟨phenyl⟩—$NH_2$, $R^2$–$R^4$ and $R^6$ are all H, and $R^5$ is —$NH_2$.

22. The method according to claim 1, wherein $R^1$ is

—⟨phenyl⟩—OH, $R^2$–$R^4$ and $R^6$ are all H, and $R^5$ is —$NH_2$.

23. The method according to claim 1, wherein $R^1$ and $R^2$ together form —CH=CH—CH=CH—, $R^3$, $R^4$ and $R^6$ are all H, and $R^5$ is —$NO_2$.

24. The method according to any of claims 1–4 and 5–23, wherein the component to be determined is a coumarin derivative.

25. The method according to claim 24, wherein the coumarin derivative is used to label an antigen or antibody in said sample.

26. A method of quantitatively determining one of a peroxidation-active substance, hydrogen peroxide or a coumarin derivative represented by the formula:

⟨structural formula with $R^1$, $R^2$, $R^3$ substituents on julolidine-coumarin scaffold⟩ wherein $R^1$ represents hydrogen, $C_{1-8}$ linear or branched alkoxy, substituted or unsubstituted phenyl, substituted or unsubstituted naphthyl, cyano, carboxyl, $C_{1-8}$ linear or branched alkoxycarbonyl, $C_{1-8}$ linear or branched alkanoyl, pyridyl or benzothiazolinyl; and $R^2$ and $R^3$ are independently hydrogen or substituted or unsubstituted $C_{1-8}$ linear or branched alkyl; or $R^1$ and $R^2$ combined together form $C_{2-4}$ alkylene or $C_{2-4}$ alkylene;

the substituted phenyl, naphthyl and alkyl are independently substituted with 1–5 cyano, halogen, amino independently substituted with 0 to 2 $C_{1-8}$ linear or branched alkyl, substituted or unsubstituted heterocyclic group (wherein the heterocyclic group is independently triazinyl, pyrazinyl, pyridyl or pyrimidinyl independently substituted with 0 to 2 cyano, halogen, amino, alkoxy, hydroxy or $C_{1-8}$ linear or branched dialkylamino), $C_{1-8}$ linear or branched alkyl, $C_{1-8}$ linear or branched alkoxy, carboxy, $C_{1-8}$ linear or branched alkoxycarbonyl and hydroxy; in a sample, comprising the steps of:

(A) selecting a sample having a known amount of two substances selected from the peroxidation-active substance, hydrogen peroxide and coumarin derivative or salt thereof;

(B) reacting said two substances with said sample having an unknown amount of the remaining substance from said peroxidation active substance, hydrogen peroxide, or coumarin derivative or salt thereof;

(C) determining the intensity of light emitted from the reacted solution; and (D) comparing the intensity of said emitted light with a calibration curve.

27. The method of claim 26 in which $R^1$ represents hydrogen, cyano, alkoxycarbonyl, alkanoyl, or carboxyl, and $R^2$ and $R^3$ are independently hydrogen or optionally substituted alkyl.

28. The method according to claim 26, wherein $R^1$ is —CN, and $R^2$ and $R^3$ are both H.

29. The method according to claim 26, wherein $R^1$ and $R^3$ are both H, and $R^2$ is —$CF_3$.

30. The method according to claim 26, wherein $R^1$ is —$COOC_2H_5$, and $R^2$ and $R^3$ are both H.

31. The method according to claim 26, wherein $R^1$ is —$COCH_3$, and $R^2$ and $R^3$ are both H.

32. The method according to claim 26, wherein $R^1$ is —$COOC(CH_3)_3$, and $R^2$ and $R^3$ are both H.

33. The method according to claim 26, wherein $R^1$ is —COOH, and $R^2$ and $R^3$ are both H.

34. The method according to any of claims 26–33, wherein the component to be determined is a coumarin derivative.

35. The method according to claim 34, wherein the coumarin derivative is used to label an antigen or antibody in said sample.

* * * * *

UNITED STATES PATENT AND TRADEMARK OFFICE
CERTIFICATE OF CORRECTION

PATENT NO. : 5,851,785

DATED : December 22, 1998

INVENTOR(S): NORHITO AOYAMA, ET AL.  Page 1 of 4

It is certified that error appears in the above-identified patent and that said Letters Patent is hereby corrected as shown below:

Title page, item

[63] RELATED U.S. APPLICATION DATA

"122,582, filed" should read --122,582, filed October 1, 1993--.

COLUMN 2

Line 40, "certain" should read --a certain--.

COLUMN 11

Line 4, "(177); should read --(1977);--.

COLUMN 13

Line 37, "an" should read --any--; and
Line 38, "well can" should be deleted.

COLUMN 14

Line 42, "to" should read --of--.

COLUMN 17

Line 27, "mixture-containinig" should read --mixture-containing--.

UNITED STATES PATENT AND TRADEMARK OFFICE
CERTIFICATE OF CORRECTION

PATENT NO. : 5,851,785
DATED : December 22, 1998
INVENTOR(S): NORHITO AOYAMA, ET AL.

It is certified that error appears in the above-identified patent and that said Letters Patent is hereby corrected as shown below:

COLUMN 18

Table 4, Under "Compound 2": "$9.26 \times 10^4$" should read --$9.27 \times 10^4$--;
under "Compound 8: "$3.11 \times 10^8$" should read --$3.11 \times 10^6$--.

COLUMN 19

Table 4, Under "Compound 9": "$2.22 \times 10^5$ should read --$2.22 \times 10^6$--;
under "Compound 12": "$2.83 \times 10^8$" should read --$2.83 \times 10^6$--;
under "Compound 14": "$1.55 \times 10^8$" should read --$1.55 \times 10^6$--;
under "Compound 31": "$1.13 \times 10^8$ $1.10 \times 10^8$" should read --$1.13 \times 10^6$ $1.10 \times 10^6$--; and
under "Compound 33": "$1.10 \times 10^8$" should read --$1.10 \times 10^6$--.

COLUMN 21

Line 8, "(PAP)" should read --(PAP))--.

UNITED STATES PATENT AND TRADEMARK OFFICE
CERTIFICATE OF CORRECTION

PATENT NO. : 5,851,785
DATED : December 22, 1998
INVENTOR(S): NORHITO AOYAMA, ET AL.

Page 3 of 4

It is certified that error appears in the above-identified patent and that said Letters Patent is hereby corrected as shown below:

COLUMN 22

Line 47, "$C_{1-8}$," should read --$C_{1-8}$--.

COLUMN 23

Line 3, "peroxidation active" should read
 --peroxidation-active--;
Line 36, "or $C_{2-4}$ alkylene" should be deleted; and
Line 59, "peroxidation active" should read
 --peroxidation-active--.

COLUMN 24

Line 11, "$R_2$-$R_4$" should read --$R^2$-$R^4$--;
Line 39, "H" should read --H,--;

Line 57, " 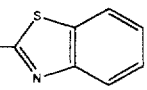 " should read -- 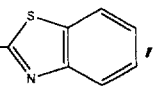, --;

Line 63, "-$CF_3$" should read ---$CF_3$,--.

UNITED STATES PATENT AND TRADEMARK OFFICE
CERTIFICATE OF CORRECTION

PATENT NO. : 5,851,785
DATED : December 22, 1998
INVENTOR(S): NORHITO AOYAMA, ET AL.

It is certified that error appears in the above-identified patent and that said Letters Patent is hereby corrected as shown below:

COLUMN 25

Line 56, "claims 1-4 and 5-23," should read --claims 1 to 23,--.

COLUMN 26

Line 17, "alky-" should read --alkeny- --; and
Line 35, "peroxidation active" should read --peroxidation-active--.

Signed and Sealed this

Eighth Day of February, 2000

Q. TODD DICKINSON

Attest:

Attesting Officer

Commissioner of Patents and Trademarks